US012337074B2

(12) United States Patent
Carroll, III et al.

(10) Patent No.: US 12,337,074 B2
(45) Date of Patent: Jun. 24, 2025

(54) LOW-COST RAPID THERMO-CHEMICAL DECONTAMINATION PROCESS FOR FACEMASKS OR OTHER PERSONAL PROTECTION EQUIPMENT (PPE) AND RELATED SYSTEM AND APPARATUS

(71) Applicant: Raytheon Company, Waltham, MA (US)

(72) Inventors: Alf L. Carroll, III, Marion, MA (US); David R. Sar, Marana, AZ (US); David D. Crouch, Riverside, CA (US); John Carcone, Portsmouth, RI (US)

(73) Assignee: Raytheon Company, Arlington, VA (US)

( * ) Notice: Subject to any disclaimer, the term of this patent is extended or adjusted under 35 U.S.C. 154(b) by 407 days.

(21) Appl. No.: 17/169,260

(22) Filed: Feb. 5, 2021

(65) Prior Publication Data

US 2021/0330842 A1   Oct. 28, 2021

Related U.S. Application Data

(63) Continuation-in-part of application No. 16/944,617, filed on Jul. 31, 2020.
(Continued)

(51) Int. Cl.
*A61L 2/20* (2006.01)
*A61L 2/18* (2006.01)

(52) U.S. Cl.
CPC ............... *A61L 2/208* (2013.01); *A61L 2/186* (2013.01); *A61L 2209/211* (2013.01)

(58) Field of Classification Search
CPC ...... A61L 2/208; A61L 2/07; A61L 2202/121; A61L 2/18
See application file for complete search history.

(56) References Cited

U.S. PATENT DOCUMENTS 3,988,930 A * 11/1976 Fitzmayer ............... G12B 17/02
219/712
4,861,956 A   8/1989 Courneya
(Continued)

FOREIGN PATENT DOCUMENTS

CN   108480290 A   9/2018
CN   108743997 A   11/2018
(Continued)

OTHER PUBLICATIONS

Non-Final Office Action dated Dec. 5, 2022 in connection with U.S. Appl. No. 16/944,617, 10 pages.
(Continued)

*Primary Examiner* — Kevin Joyner (57) ABSTRACT

A system for decontaminating personal protection equipment includes a microwave oven and a decontamination apparatus configured to be placed in and heated by the microwave oven. The decontamination apparatus includes a containment vessel having an interior space configured to be sealed. The decontamination apparatus also includes one or more stands within the interior space, where the one or more stands are configured to receive and hold one or more pieces of personal protection equipment to be heated by the microwave oven and decontaminated within the interior space. The decontamination apparatus further includes a pressure-relief valve configured to be opened to release a pressure within the interior space.

8 Claims, 9 Drawing Sheets

Related U.S. Application Data (60) Provisional application No. 63/015,000, filed on Apr. 24, 2020.

(56) References Cited

U.S. PATENT DOCUMENTS

| | | | |
|---|---|---|---|
| 5,108,701 | A | 4/1992 | Zakaria et al. |
| 5,117,809 | A | 6/1992 | Scaringe et al. |
| 8,802,023 | B1 | 8/2014 | Lewis et al. |
| 9,222,665 | B2 | 12/2015 | Halas et al. |
| 9,878,061 | B2 | 1/2018 | Shur et al. |
| 10,654,726 | B2 | 5/2020 | Nigrelli |
| 2001/0036670 | A1* | 11/2001 | Fryer ............... G01N 31/226 422/62 |
| 2003/0206827 | A1* | 11/2003 | Lin ..................... A61L 2/208 422/33 |
| 2004/0040586 | A1 | 3/2004 | Kumar |
| 2007/0186579 | A1 | 8/2007 | Barker |
| 2007/0253859 | A1 | 11/2007 | Hill |
| 2008/0251063 | A1* | 10/2008 | Palena ................ F24V 30/00 126/263.09 |
| 2013/0280134 | A1* | 10/2013 | Hoffman ............... A61L 2/07 422/114 |
| 2014/0224687 | A1* | 8/2014 | Schuster ............. A61B 50/30 206/363 |
| 2016/0264332 | A1* | 9/2016 | Rapparini .......... B65D 77/225 |
| 2016/0352022 | A1 | 12/2016 | Thomson et al. |
| 2018/0140732 | A1 | 5/2018 | Liu |

FOREIGN PATENT DOCUMENTS

| | | | |
|---|---|---|---|
| CN | 109959175 A | 7/2019 | |
| CN | 111012933 A | 4/2020 | |
| DE | 4328589 A1 | 3/1995 | |
| GB | 2507724 A * | 5/2014 | ............... A61L 2/07 |
| WO | 2017223224 A1 | 12/2017 | |

OTHER PUBLICATIONS

International Search Report and Written Opinion of the International Searching Authority in connection with International Patent Application No. PCT/US2021/070215 issued Jun. 15, 2021, 10 pages.

Bioquell UK Ltd., "Bioquell | Clarus C," Product Sheet, LS001-MKT-011 Rev 1, 2012, 2 pages.

Carlson et al., "Solar powered water purification system," Mechanical Engineering Senior Theses, Santa Clara University, Jan. 2012, 160 pages.

Chandler, "Sterilizing with the sun: Solar concentrating system could replace fuel-powered or electric devices in remote villages," Phys.org News, Feb. 2013, 3 pages.

"Food Cooking Medical Sterilization and Ice Making (adsorption process) with the Soleil-Vapeur Solar Thermal Steam Unit," soleil-vapeur.org, Oct. 2014, 4 pages.

Heimbuch et al., "A Pandemic Influenza Preparedness Study: Use of Energetic Methods to Decontaminate Filtering Facepiece Respirators Contaminated with H1N1 Aerosols and Droplets," Jun. 2012, 11 pages.

Lowe et al., "N95 Filtering Facepiece Respirator Ultraviolet Germicidal Irradiation (UVGI) Process for Decontamination and Reuse," Nebraska Medicine, Apr. 2020, 19 pages.

Lu, "Portable device uses solar power to sterilise medical equipment," NewScientist, Nov. 2020, 6 pages.

Mechler, "Mask Disinfection & Sterilization for Viruses," https://consteril.com/covid-19-pandemic-disinfection-and-sterilization-of-face-masks-for-viruses, Apr. 2020, 19 pages.

"Parabolic Solar Trough—Thermal Water Heater," Parabolic Trough Concentrated Solar Power, Dec. 2020, 6 pages.

"Preppers Peak Solar Cooker Kettle for Camping Outdoor Travel with Solar Technology," Kettles for Water, Dec. 2020, 2 pages.

Roel, "350mm f/4 lightweight truss Dobson (airline transportable)," DIY Astronomer, Stargazers Lounge, Dec. 2013, 23 pages.

Sherwin, "GoSun Sport: Portable, High Efficiency Solar Cooker," Kickstarter, May 2019, 29 pages.

"Sterilizing medical tools off the grid using solar heat," Innovation Toronto, Dec. 2020, 5 pages.

U.S. Department of Labor, "Hospital Respiratory Protection Program Toolkit Resources for Respirator Program Administrators," Occupational Safety and Health Administration (OSHA), DHHS (NIOSH) Publication No. 2015-117, OSHA Publication No. 3767, May 2015, 96 pages.

Crouch et al., "Solar-Heater Thermo-Chemical Decontamination System for Facemasks or Other Personal Protection Equipment (PPE)," U.S. Appl. No. 16/986,761, filed Aug. 6, 2020, 32 pages.

Crouch et al., "Containment Vessels for Rapid Thermo-Chemical Decontamination of Facemasks or Other Personal Protection Equipment (PPE)," U.S. Appl. No. 16/944,617, filed Jul. 31, 2020, 43 pages.

Crouch et al., "Ultra-Compact Portable Solar-Powered Thermo-Chemical Decontamination System and Method," U.S. Appl. No. 17/124,208, filed Dec. 16, 2020, 36 pages.

Feenstra et al., "Low-Cost, Portable, Flameless-Heater-Powered Thermo-Chemical Decontamination System for Facemasks and Other Types of Personal Protection Equipment (PPE)," U.S. Appl. No. 17/182,067, filed Feb. 22, 2021, 37 pages.

Non-Final Office Action dated Aug. 7, 2023 in connection with U.S. Appl. No. 16/944,617, 13 pages.

Final Office Action dated Mar. 28, 2023 in connection with U.S. Appl. No. 16/944,617, 13 pages.

Non-Final Office Action dated Feb. 20, 2024 in connection with U.S. Appl. No. 16/944,617, 14 pages.

The Kombucha Company, "Step 5—IBC Rainwater Harvesting System—Connecting and Venting Tanks," YouTube video, https://www.youtube.com/watch?v=9xj-Fus7R7Q, Oct. 2014, 2 pages.

Final Office Action dated Aug. 1, 2024 in connection with U.S. Appl. No. 16/944,617, 15 pages.

Communication pursuant to Article 94(3) EPC dated Oct. 28, 2024 in connection with European Patent Application No. 21714604.2, 3 pages.

Communication pursuant to Article 94(3) EPC dated Jan. 15, 2025, in connection with European Patent Application No. 21724831.9, 3 pages.

HipCooking, "Pressure Cooker Accessory: Steamer Basket," https://www.hippressurecooking.com/pressure-cooker-accessory-steamer-basket/, May 2013, 13 pages.

Communication pursuant to Article 94(3) EPC dated Apr. 7, 2025 in connection with European Patent Application No. 21714604.2, 5 pages.

* cited by examiner

LOW-COST RAPID THERMO-CHEMICAL DECONTAMINATION PROCESS FOR FACEMASKS OR OTHER PERSONAL PROTECTION EQUIPMENT (PPE) AND RELATED SYSTEM AND APPARATUS

CROSS-REFERENCE TO RELATED APPLICATIONS AND PRIORITY CLAIM

This application claims priority under 35 U.S.C. § 119(e) to U.S. Provisional Patent Application No. 63/015,000 filed on Apr. 24, 2020, which is hereby incorporated by reference in its entirety.

This application also claims priority under 35 U.S.C. § 120 as a continuation-in-part of U.S. patent application Ser. No. 16/944,617 filed on Jul. 31, 2020, which is hereby incorporated by reference in its entirety.

TECHNICAL FIELD

This disclosure relates generally to medical decontamination processes. More specifically, this disclosure relates to a low-cost rapid thermo-chemical decontamination process for facemasks or other personal protection equipment (PPE) and related system and apparatus.

BACKGROUND

A dangerous gap has developed in the available supply of disposable facemasks, such as N95/KN95/N99/N100/P100 surgical masks, and other personal protection equipment (PPE), such as surgical gowns, booties, and gloves, as a result of the COVID-19 pandemic. Accelerating demand has outstripped the ability of the supply chain to keep pace. As a result, medical staff are (among other things) routinely forced to use a large amount of personal protection equipment and, in some cases, wear the same masks or other personal protection equipment to treat multiple patients, which poses a cross-contamination hazard to patients and medical personnel. An additional risk is mask "breakthrough" in which contaminants eventually diffuse through a mask and infect the wearer.

SUMMARY

This disclosure provides a low-cost rapid thermo-chemical decontamination process for facemasks or other personal protection equipment (PPE) and related system and apparatus.

In a first embodiment, a method includes soaking one or more pieces of personal protection equipment in a disinfectant. The method also includes placing the one or more pieces of personal protection equipment within a containment vessel and sealing the containment vessel. The method further includes decontaminating the one or more pieces of personal protection equipment by heating the one or more pieces of personal protection equipment in the sealed containment vessel. In addition, the method includes opening a pressure-relief valve of the containment vessel.

In a second embodiment, an apparatus includes a containment vessel having an interior space configured to be sealed. The apparatus also includes one or more stands within the interior space, where the one or more stands are configured to receive and hold one or more pieces of personal protection equipment to be heated and decontaminated within the interior space. The apparatus further includes a pressure-relief valve configured to be opened to release a pressure within the interior space.

In a third embodiment, a system for decontaminating personal protection equipment includes a microwave oven and a decontamination apparatus configured to be placed in and heated by the microwave oven. The decontamination apparatus includes a containment vessel having an interior space configured to be sealed. The decontamination apparatus also includes one or more stands within the interior space, where the one or more stands are configured to receive and hold one or more pieces of personal protection equipment to be heated by the microwave oven and decontaminated within the interior space. The decontamination apparatus further includes a pressure-relief valve configured to be opened to release a pressure within the interior space.

Other technical features may be readily apparent to one skilled in the art from the following figures, descriptions, and claims.

BRIEF DESCRIPTION OF THE DRAWINGS

For a more complete understanding of this disclosure, reference is made to the following description, taken in conjunction with the accompanying drawings, in which.

DETAILED DESCRIPTION

FIGS. 1 through 11, described below, and the various embodiments used to describe the principles of the present disclosure are by way of illustration only and should not be construed in any way to limit the scope of the disclosure. Those skilled in the art will understand that the principles of the present disclosure may be implemented in any type of suitably arranged device or system.

As noted above, a dangerous gap has developed in the available supply of personal protection equipment (PPE), such as disposable facemasks (like N95/KN95/N99/N100/P100 surgical masks), surgical gowns, booties, and gloves, as a result of the COVID-19 pandemic. Disposable facemasks are sometimes referred to as surgical respirators. Accelerating demand has outstripped the ability of the supply chain to keep pace. As a result, medical staff are (among other things) routinely forced to use a large amount of personal protection equipment and, in some cases, wear the same masks or other personal protection equipment to treat multiple patients. This poses a cross-contamination hazard to patients and medical personnel and poses an additional risk related to mask "breakthrough" in which contaminants eventually diffuse through a mask and infect the wearer. Under normal circumstances, facemasks, surgical gowns, booties, gloves, and other personal protection equipment may typically be disposable, meaning they are worn once and discarded. However, when supplies run low (such as during a pandemic), it may be necessary or desirable to decontaminate and reuse facemasks, surgical gowns, booties, gloves, and other personal protection equipment.

Some approaches for decontaminating personal protection equipment involve the use of hydrogen peroxide ($H_2O_2$) vapor to decontaminate the personal protection equipment. However, these approaches may take an extended period of time (such as about 8 hours) to complete, which can be problematic in environments where a large amount of personal protection equipment is used. These approaches may also require high concentrations of hydrogen peroxide (such as 35% compared to about 3% to 6% over-the-counter solutions), which can be toxic and potentially explosive. Other approaches for decontaminating personal protection equipment involve the use of ultraviolet germicidal irradiation in which the personal protection equipment is illuminated using ultraviolet light, which can deactivate or kill bacteria and viruses. However, inner layers of a facemask or other personal protection equipment may not receive a high enough dose of ultraviolet radiation, and light transmittance varies among equipment. Also, straps or other structures of personal protection equipment can present a residual contamination risk and may require a secondary decontamination process, and it is often challenging to ensure that all surfaces/layers of personal protection equipment are completely decontaminated due to shadowing effects. Still other approaches for decontaminating personal protection equipment involve the use of microwave-generated or solar-generated steam, which is an effective technique for decontaminating medical instruments and other materials used every day in surgeries, procedures, and patient services. However, when used with disposable personal protection equipment, microwave-generated or solar-generated steam runs the risk of overheating the personal protection equipment, causing damage or degradation. If a facemask is even slightly deformed by heating to excessive temperatures, it can lose its ability to protect the wearer and must be discarded.

This disclosure provides low-cost systems and methods that use heating in combination with a low-concentration hydrogen peroxide solution or other disinfectant to rapidly and simultaneously decontaminate personal protection equipment in order to facilitate safe reuse of the personal protection equipment, such as during pandemic-induced shortages. Some embodiments of the systems and methods here can maximize the use of commercial off-the-shelf (COTS) equipment and chemicals already present in a medical setting, such as a standard hospital or a mobile Army surgical hospital (MASH) setting. Thus, various equipment and chemicals are typically already available in quantity in the medical setting. These systems and methods can also limit peak temperatures of the personal protection equipment to a suitable range, such as about 65° C. to about 80° C., to prevent damage to the personal protection equipment or degradation of the personal protection equipment's fit or function while being adequate to deactivate or kill pathogens or otherwise decontaminate the personal protection equipment. In addition, the systems and methods may present little or no hazard to medical staff. The systems and methods thereby combine chemical and radio frequency (RF) or other heat decontamination in order to safely and effectively decontaminate personal protection equipment using components that are likely already available in a particular medical setting.

In some embodiments, the process for decontaminating facemasks or other personal protection equipment involves soaking the personal protection equipment in a low-concentration hydrogen peroxide solution (such as an about 3% to about 6% hydrogen peroxide solution or other hydrogen peroxide solution) or other disinfectant that is safe for everyday use. The soaking can help to prevent the facemasks or other personal protection equipment from overheating during higher-temperature periods of the decontamination process. The personal protection equipment is then placed inside a containment vessel, which is sealed in order to keep moisture, hydrogen peroxide or other disinfectant, and contaminants inside the containment vessel during the decontamination process. Optionally, at least one reservoir of additional low-concentration hydrogen peroxide solution or other disinfectant may be positioned under the personal protection equipment or otherwise within the containment vessel to help provide adequate vapor in the containment vessel and around the personal protection equipment during decontamination. Also, the containment vessel can optionally be heated and then sealed in order to replace much or all of the atmospheric air inside the containment vessel with vapor, such as water and hydrogen peroxide or other disinfectant vapor. The containment vessel is heated to a raised temperature, such as about 65° C. to about 80° C. (like about 70° C.), and maintained at the raised temperature for a period of time to decontaminate the personal protection equipment inside the containment vessel.

In some embodiments, the containment vessel can be heated in a microwave oven or other source of microwave radiation. In other embodiments, the containment vessel can be heated in other ways, such as via solar radiation or on a stovetop. However heated, the combination of heat and heat-activated disinfectant deactivates or destroys bio-contaminants (such as bacteria and viruses) faster and at a lower temperature than either heat or disinfectant alone. Once the decontamination cycle is complete, a pressure-relief valve, such as in a lid of the containment vessel, can be opened, and the containment vessel may be reheated to dry the personal protection equipment (while vapor in the containment vessel escapes through the valve). Other approaches for drying the personal protection equipment may also be used here.

In this way, synergy is achieved by attacking contaminants with both moist heating and hydrogen peroxide or other disinfectant, yielding faster and more effective decontamination than either approach used alone. Also, the lower-temperature decontamination process protects facemasks or other personal protection equipment from damage or degradation, and the use of materials such as about 3% to about 6% hydrogen peroxide solution or other disinfectant avoids toxic concentrations, potential explosiveness, or other problems of higher concentrations. Moreover, the presence of metal nose strips, staples, or other metal components of the personal protection equipment will not cause damage to the equipment or their rubber straps during the decontamination process. This may be achieved using lower-power operation (to limit temperature increases) and the presence of moisture in the containment vessels, which helps to prevent the metal components from overheating and damaging the personal protection equipment. This may also be achieved by distributing and orienting the personal protection equipment to reduce or minimize the risk of arcing between metal components while increasing or maximizing the number or amount of equipment that can fit into the available volume (to reduce or minimize the decontamination cost per piece of equipment).

FIGS. 1 through 4 illustrate an example portable thermochemical decontamination containment vessel 100 in accordance with this disclosure. As shown in FIGS. 1 through 4, the containment vessel 100 generally includes a body 102 and a lid 104 configured to be secured to the body 102. The body 102 and the lid 104 collectively define an interior space or volume 106 into which personal protection equipment can be placed. A seal 108 may be positioned between the body 102 and the lid 104 in order to help isolate or seal the volume 106 when the lid 104 is secured to the body 102. This helps to retain water, hydrogen peroxide or other disinfectant, contaminants, or other materials inside the containment vessel 100 until a decontamination process is completed. In some cases, the containment vessel 100 may take the form of a modified, customized, or other microwavable pressure cooker or similar type of device, although this is not necessarily required.

The body 102 and the lid 104 of the containment vessel 100 may be formed from any suitable material(s). In some embodiments, the body 102 and the lid 104 may be formed from ruggedized plastic or other material(s) that can be used in a microwave oven. This may include one or more materials having a low loss tangent at 915 MHz and/or 2.45 GHz and a suitable glass transition or softening temperature, such as high-density polyethylene, polymethylpentene, polypropylene, or polysulfone. Other materials may include those normally used in food preparation, such as metal, tempered glass, or ceramic. The body 102 and the lid 104 may also be formed in any suitable manner, such as additive manufacturing, injection molding, casting, machining, or other suitable technique. The containment vessel 100 overall may have any suitable size, shape, and dimensions, and each of the body 102 and the lid 104 may have any suitable size, shape, and dimensions. As a particular example, the containment vessel 100 may have an interior volume 106 of about 3.4 quarts, a height of about 7.75 inches, and a generally cylindrical shape, although other capacities, sizes, and shapes may be used. In some cases, the body 102 and the lid 104 may represent interlocking portions so that the lid 104 can be mechanically coupled to and released from the body 102, such as via rotation of the lid 104. The seal 108 includes any suitable structure configured to seal the interior space of the containment vessel 100, such as a rubber or other O-ring.

One or more pressure-relief valves 110 can be used with the containment vessel 100. The pressure-relief valve 110 allows the interior volume 106 of the containment vessel 100 to be sealed during heating of the equipment, thereby increasing the pressure within the containment vessel 100 during the heating. Among other things, this helps to keep water and hydrogen peroxide or other disinfectant vapor surrounding the personal protection equipment during a decontamination process. Once the decontamination process is completed, the pressure-relief valve 110 can be opened in order to allow excess pressure in the containment vessel 100 to be relieved. At that point, the personal protection equipment can be removed from the containment vessel 100 for drying, or the containment vessel 100 can be reheated (with the pressure-relief valve 110 opened) to dry the personal protection equipment. Each pressure-relief valve 110 includes any suitable structure configured to be selectively opened and closed to provide or block a pathway for pressure to escape from the interior volume 106 of the containment vessel 100. In this example, the pressure-relief valve 110 defines a passageway 112 leading from an external environment into the interior volume 106 of the containment vessel 100 and a knob 114 that can be manually rotated to selectively block and unblock the passageway 112. However, the pressure-relief valve 110 may have any other suitable form.

In some cases, the pressure-relief valve 110 may include, be integrated with, or otherwise be used in conjunction with a filter 116. In this example, the filter 116 is shown as be used within the pressure-relief valve 110, although the filter 116 may be positioned at any other suitable location within or outside the pressure-relief valve 110. Each filter 116 may be used to filter air or other fluid passing out of the containment vessel 100, such as during or after heating of the containment vessel 100. For instance, after being placed in a microwave oven or otherwise heated for a specified period of time, the pressure-relief valve(s) 110 may be opened, and the filter(s) 116 may filter air passing out of the containment vessel 100. Among other things, this may help to prevent contamination of a microwave oven, stovetop, oven, or other components used with or around the containment vessel 100.

Each filter 116 includes any suitable structure configured to remove contaminants or other materials from fluid, such as a HEPA filter. In some embodiments, each filter 116 is implemented by bonding or otherwise securing an adapter to the containment vessel 100, where the adapter is configured to receive a HEPA or other filter canister. As a particular example, the adapter may be threaded for attachment to the containment vessel 100, and an O-ring or other seal can be used to seal the adapter to the containment vessel 100. However, any other suitable implementation of the filter 116 may be used here.

Note that this example includes one pressure-relief valve 110 and one filter 116, although the containment vessel 100 may include more than one pressure-relief valve 110 and more than one filter 116. Also note that the pressure-relief valve(s) 110 and filter(s) 116 may be positioned at any suitable location(s) of the containment vessel 100 and may or may not be positioned on the lid 104 of the containment vessel 100. In addition, note that the use of integrated pressure-relief valves 110 and filters 116 is not required and that, for instance, at least one pressure-relief valve 110 and at least one separate filter 116 may be used (or the filter or filters 116 may be omitted completely).

Figure 1:
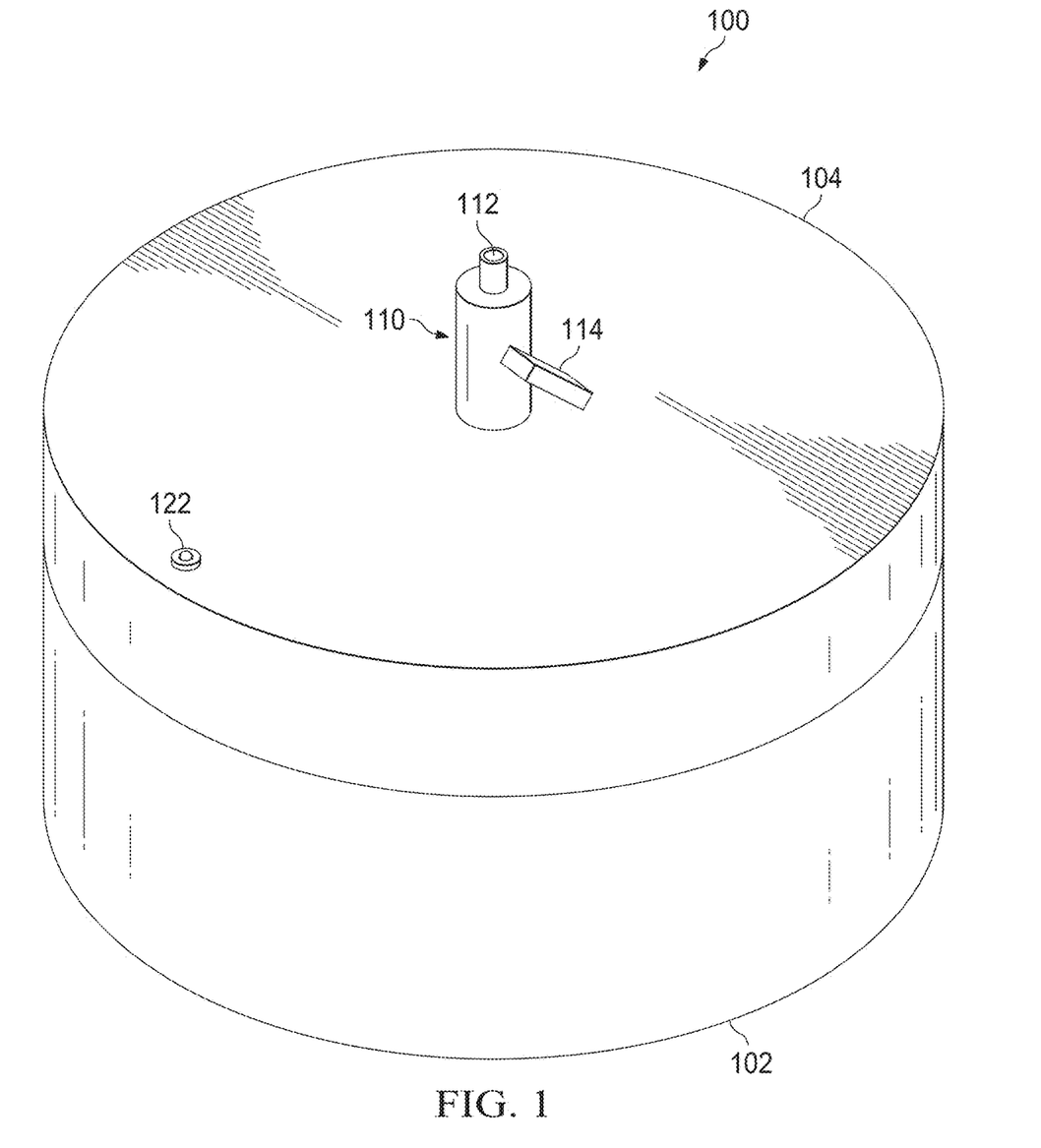
FIGS. 1 through 4 illustrate an example portable thermo-chemical decontamination containment vessel in accordance with this disclosure.
Figure 2:
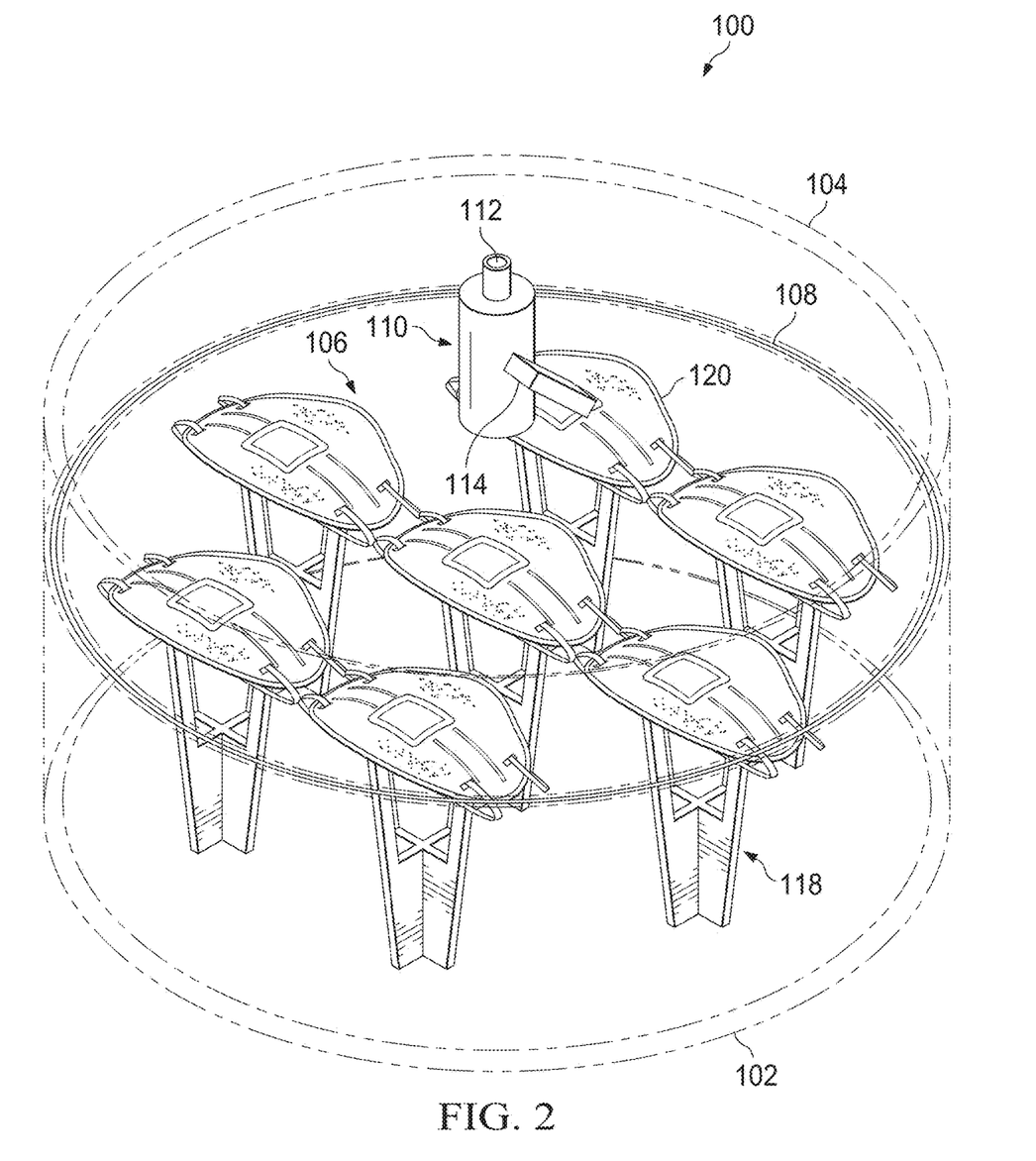
Figure 3:
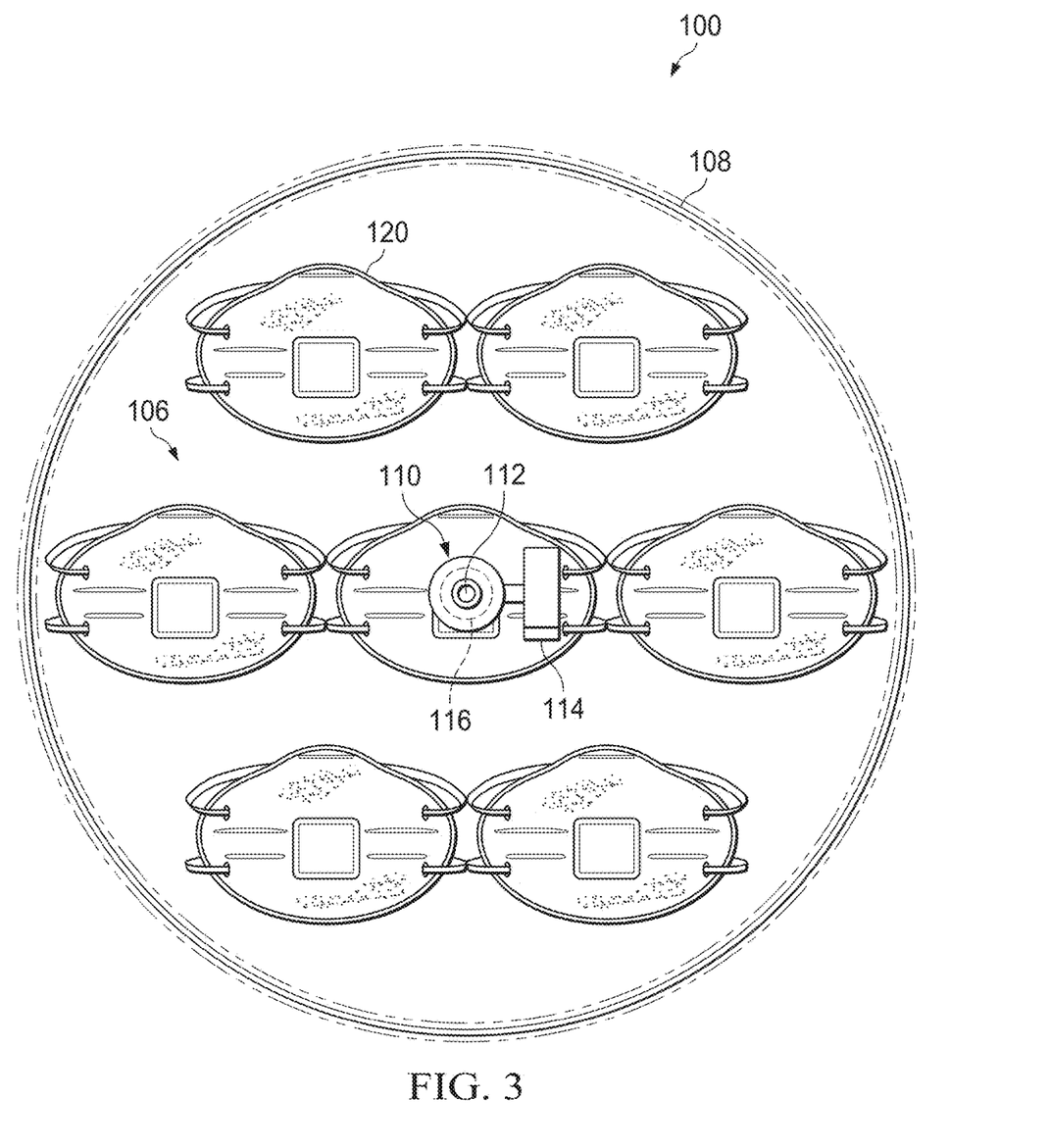
Figure 4:
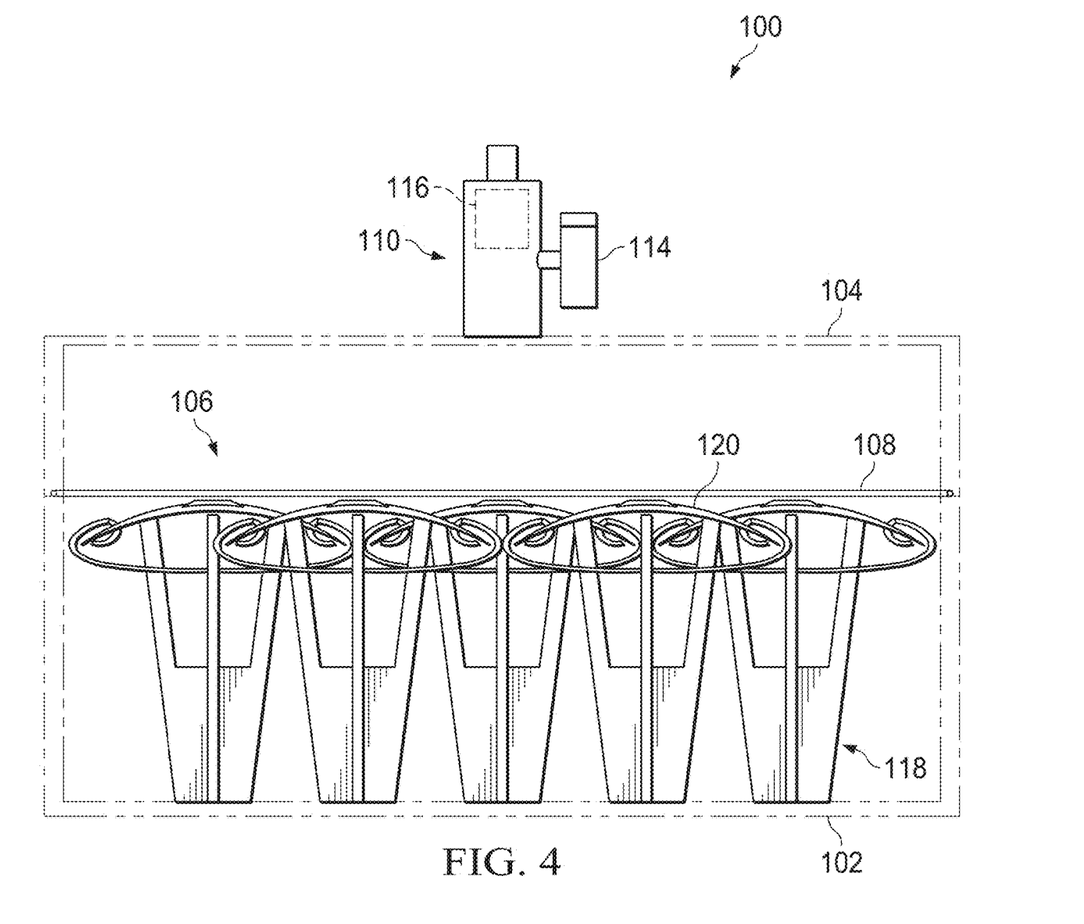

As shown in FIGS. 2 and 4, multiple stands 118 are provided and used to hold multiple pieces of personal protection equipment 120. The stands 118 hold the personal protection equipment 120 above a bottom surface of the interior volume 106. This may allow, for example, most or all surfaces of the personal protection equipment 120 to be exposed to hydrogen peroxide or other disinfectant vapor during a decontamination process. This may also allow at least one reservoir of liquid (such as a low-concentration hydrogen peroxide solution or other disinfectant) to be placed within the interior volume 106 of the containment vessel 100 and remain underneath the stands 118. When the liquid in the containment vessel 100 is heated, vaporized liquid can travel upward and surround the personal protection equipment 120 to facilitate decontamination of the personal protection equipment 120. The stands 118 may be formed from any suitable material(s), such as metal or ruggedized plastic. The stands 118 may also be formed in any suitable manner, such as additive manufacturing, injection molding, casting, machining, or other suitable technique. Each of the stands 118 may have any suitable size, shape, and dimensions.

In this example, the pieces of personal protection equipment 120 include multiple facemasks, such as N95/KN95/N99/N100/P100 surgical masks. In this particular example, there are three rows having a total of seven stands 118 that can receive seven facemasks, where the rows are offset from one another. However, the exact number and arrangement of the stands 118 and personal protection equipment 120 can vary as needed or desired, such as when other numbers of offset or non-offset rows of stands 118 are provided. However arranged, the heating of the interior volume 106 of the containment vessel 100, along with the presence of the heat-activated hydrogen peroxide or other disinfectant in and around the personal protection equipment 120, helps to facilitate faster and more effective decontamination of the personal protection equipment 120.

In some embodiments, a decontamination process involving the containment vessel 100 may occur as follows. A suitable amount of personal protection equipment 120 can be placed on the stands 118, such as an amount of personal protection equipment 120 that partially or substantially fills the interior volume 106 of the containment vessel 100. The personal protection equipment 120 may be soaked in liquid, such as a low-concentration hydrogen peroxide solution or other disinfectant, prior to be placed on the stands 118. A suitable amount of liquid, such as low-concentration (like 3% to 6%) hydrogen peroxide solution or other disinfectant, can also optionally be placed in the volume 106 of the containment vessel 100. For instance, the amount of liquid may be adequate to cover the bottom surface of the interior volume 106 of the containment vessel 100. The lid 104 can then be secured to the body 102 of the containment vessel 100. In some cases, the pressure-relief valve(s) 110 may initially be opened, and the containment vessel 100 can be heated (such as in a microwave oven, on a stovetop, in an oven, using solar radiation, or in any other suitable manner) to allow air in the containment vessel 100 to be substantially replaced with vapor, after which the pressure-relief valve(s) 110 may be closed and the containment vessel 100 can be reheated. In other cases, the pressure-relief valve(s) 110 may initially be closed, and the containment vessel 100 can be heated (such as in a microwave oven, on a stovetop, in an oven, using solar radiation, or in any other suitable manner) with the pressure-relief valve(s) 110 in the closed position. In either case, once the containment vessel 100 is sealed using the pressure-relief valve(s) 110, the heating may continue for a specified time period, and the heating can heat the personal protection equipment 120 to a temperature within a relatively-low temperature range, such as about 65° C. to about 80° C., to prevent damage to the personal protection equipment 120 while decontaminating the personal protection equipment 120.

Once this part of the process is completed, the personal protection equipment 120 can be dried, which may occur in any suitable manner. For instance, in some cases, the personal protection equipment 120 may be removed from the containment vessel 100 and allowed to air dry (such as on a rack), or the personal protection equipment 120 may be removed from the containment vessel 100 and mechanically dried using a hair dryer or other heat or air source (assuming an adequately-reliable or accessible power source is available). In other cases, the pressure-relief valve(s) 110 can be opened, and the containment vessel 100 can again be heated (possibly in the same or similar manner as the first heating) so that moisture within the containment vessel 100 can escape and allow drying of the personal protection equipment 120. Any other suitable approach for drying the personal protection equipment 120 may also be used here.

In some embodiments, a physical indicator may be used to identify when the personal protection equipment in the containment vessel 100 has been heated to a desired temperature range for a desired amount of time in order to complete a decontamination process. For example, a microwave-safe pop-up thermometer 122 or other indicator (such as one similar to those used in turkeys to indicate when cooking is completed) may be incorporated into the containment vessel 100. As a particular example, a red plastic cap or other component might protrude above the surface of the containment vessel 100 when the desired temperature and time has been reached and decontamination has been completed.

Although FIGS. 1 through 4 illustrate one example of a portable thermo-chemical decontamination containment vessel 100, various changes may be made to FIGS. 1 through 4. For example, the sizes, shapes, and dimensions of the containment vessel 100 and its individual components can vary as needed or desired. Also, the number and placement of various components of the containment vessel 100 can vary as needed or desired. In addition, the containment vessel 100 may be used in any other suitable decontamination process and is not limited to the specific processes described above.

Figure 5:
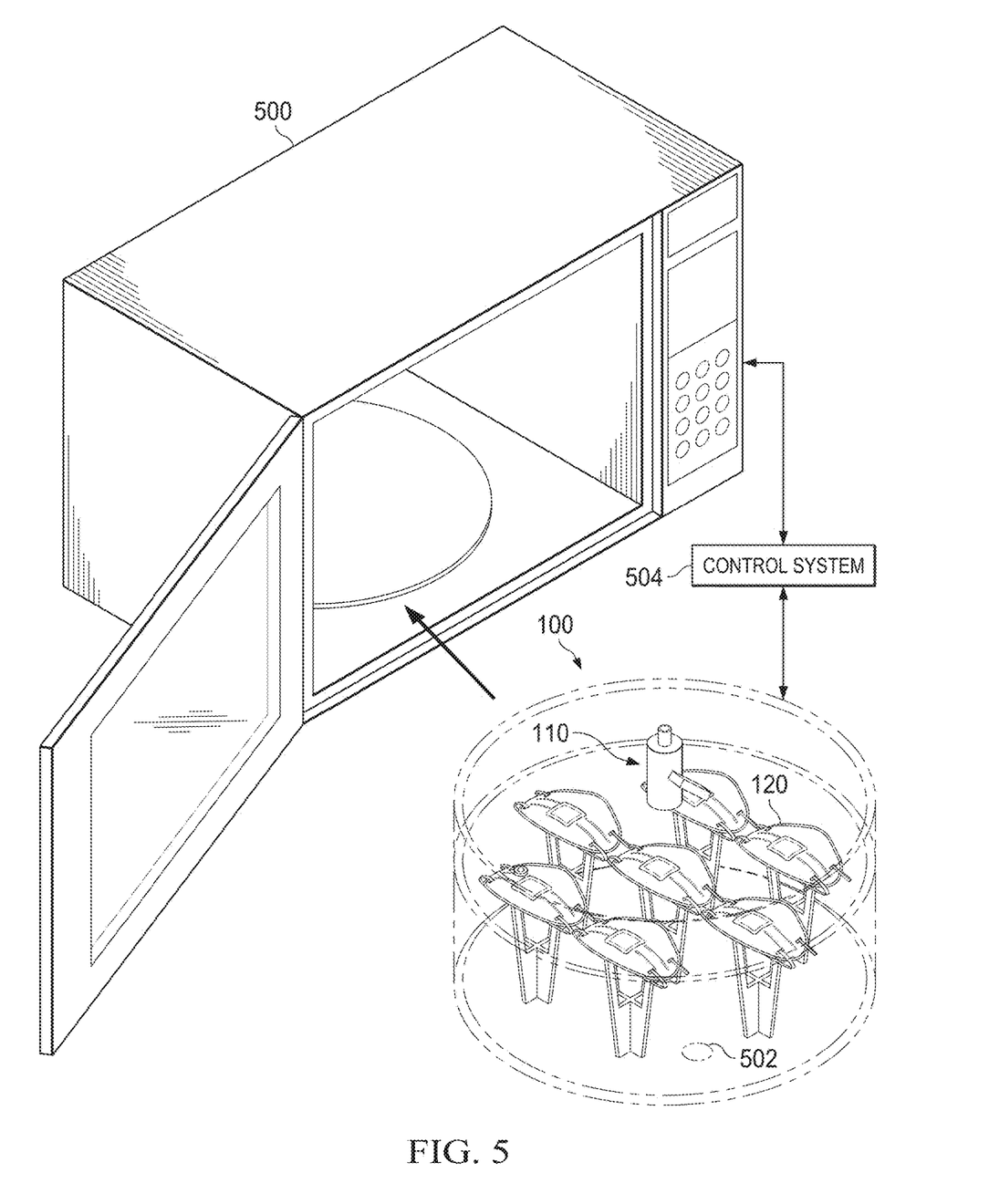
FIG. 5 illustrates an example use of a portable thermo-chemical decontamination containment vessel in accordance with this disclosure.

FIG. 5 illustrates an example use of a portable thermo-chemical decontamination containment vessel 100 in accordance with this disclosure. As shown in FIG. 5, multiple pieces of personal protection equipment 120 have been placed inside the containment vessel 100, and the lid 104 of the containment vessel 100 has been secured to the body 102 of the containment vessel 100. The containment vessel 100 is being placed within a microwave oven 500, which provides the heating action used to heat the containment vessel 100 and the personal protection equipment 120 and liquid inside the containment vessel 100.

Depending on the process, the containment vessel 100 may facilitate a two-cycle process. In the two-cycle process, a first stage involves sealing the containment vessel 100 by closing the pressure-relief valve(s) 110 and heating the containment vessel 100, where water and hydrogen peroxide or other disinfectant remain inside the containment vessel 100 to maximize the speed and effectiveness of the decontamination process. A second stage involves opening the pressure-relief valve(s) 110 and again heating the containment vessel 100 so that vapor can escape while the personal protection equipment 120 dries.

In other cases, the containment vessel 100 may facilitate a three-cycle process. In the three-cycle process, a first stage involves heating the containment vessel 100 while the containment vessel 100 is not sealed, meaning the pressure-relief valve(s) 110 can be partially or completely opened. This allows air within the containment vessel 100 to be substantially or completed replaced by vapor, such as water and hydrogen peroxide or other disinfectant vapor. A second stage involves sealing the containment vessel 100 by closing the pressure-relief valve(s) 110 and reheating the containment vessel 100, where water and hydrogen peroxide or other disinfectant remain inside the containment vessel 100 to maximize the speed and effectiveness of the decontamination process. A third stage involves opening the pressure-relief valve(s) 110 and again heating the containment vessel 100 so that vapor can escape while the personal protection equipment 120 dries.

In either approach, this facilitates separate decontamination and drying cycles, where water and hydrogen peroxide or other disinfectant are retained during the decontamination cycle and allowed to escape during the drying cycle. In addition, an optional HEPA filter or other filter 116 can be placed at the outlet of each pressure-relief valve 110 or otherwise used with each pressure-relief valve 110 as an added precaution if necessary or desirable. For instance, this may help to reduce or prevent contamination of the microwave oven 500.

Note that the personal protection equipment 120 can be dried outside the containment vessel 100 if needed or desired. Thus, there may be no need for the final stage of the decontamination process to occur inside the microwave oven 500. Also note that rotation of the containment vessel 100 may or may not occur during heating, so the containment vessel 100 may be used in non-rotating microwave ovens 500 or with other heat sources that lack rotation capabilities. Of course, nothing prevents the containment vessel 100 from being used in a microwave oven 500 or with another heat source that includes rotation capabilities. However, the ability to support non-rotational use of the containment vessel 100 may allow larger or non-cylindrical versions of the containment vessel to be designed and used, since requiring rotation of the containment vessel may limit the maximum size of the containment vessel in certain applications (like with rotating microwave ovens 500).

If needed or desired, at least one temperature sensor 502 (such as an infrared sensor or temperature probe) may be used within the containment vessel 100 in order to measure the temperatures of the personal protection equipment within the containment vessel 100. The measured temperatures of the personal protection equipment may be fed back to a user or a control system 504 (which may be integrated without or outside the microwave oven 500) in order to facilitate control of the power level, time, or other characteristics of the heating of the containment vessel 100. In some instances, this type of approach may be used with a customized microwave oven 500 in which feedback from the temperature sensor(s) can be used to dynamically control the operation of the microwave oven 500. In other instances, an off-the-shelf microwave oven 500 may be used, and little or no feedback may be provided to the microwave oven 500 (although feedback might be provided to a user or another device outside the microwave oven 500 in some cases).

These approaches are scalable and can support various implementations, such as rapid deployments using commercial microwave ovens to custom systems designed for high throughput. These approaches also allow local scaling, such as when hospitals or nursing homes leverage neighborhood restaurants to rapidly decontaminate personal protection equipment.

If a conventional off-the-shelf microwave oven 500 is used without any control logic for decontamination, various approaches may be used to calibrate the microwave oven 500 or otherwise ensure that personal protection equipment is heated to an appropriate temperature range and maintained there for a period needed to complete the decontamination process without overheating. Thus, for example, test strips of wetted material can be placed inside a containment vessel 100, and temperatures of the test strips can be monitored in order to identify desired settings for a particular microwave oven 500. The effectiveness of the heating and hydrogen peroxide or other disinfectant can also be evaluated, such as by using standard autoclave test pathogens, and compared with known susceptibility curves for both test pathogens and specific pathogens of concern (such as COVID-19). In other instances, the microwave oven 500 may be set to a relatively low power and activated for a prolonged period of time, and a user may constantly monitor the pop-up indicator and turn the microwave oven 500 off when the pop-up indicator is triggered. In general, there are a number of ways in which conventional (non-customized) microwave ovens 500 can be used here.

Note that while various types of personal protection equipment, including surgical facemasks, can be decontaminated using the approaches described here, particular types of personal protection equipment may be excluded from use in certain circumstances. For example, some facemasks use an active carbon filter layer or other active carbon filter element. These types of facemasks may not be decontaminated using microwave radiation from a microwave oven 500, as the active carbon in the filter element may overheat and/or combust and damage the attached personal protection equipment. However, these types of facemasks may be decontaminated if heating is provided via another mechanism, such as solar heating. As a particular example, the containment vessel 100 may be used with the solar heating systems described in U.S. patent application Ser. No. 16/986,761 filed on Aug. 6, 2020 (which is hereby incorporated by reference in its entirety).

Although FIG. 5 illustrates one example use of a portable thermo-chemical decontamination containment vessel 100, various changes may be made to FIG. 5. For example, the containment vessel 100 may be heated using any other suitable heat source, such as a stovetop, an oven, or a solar radiation collector.

Figure 6:
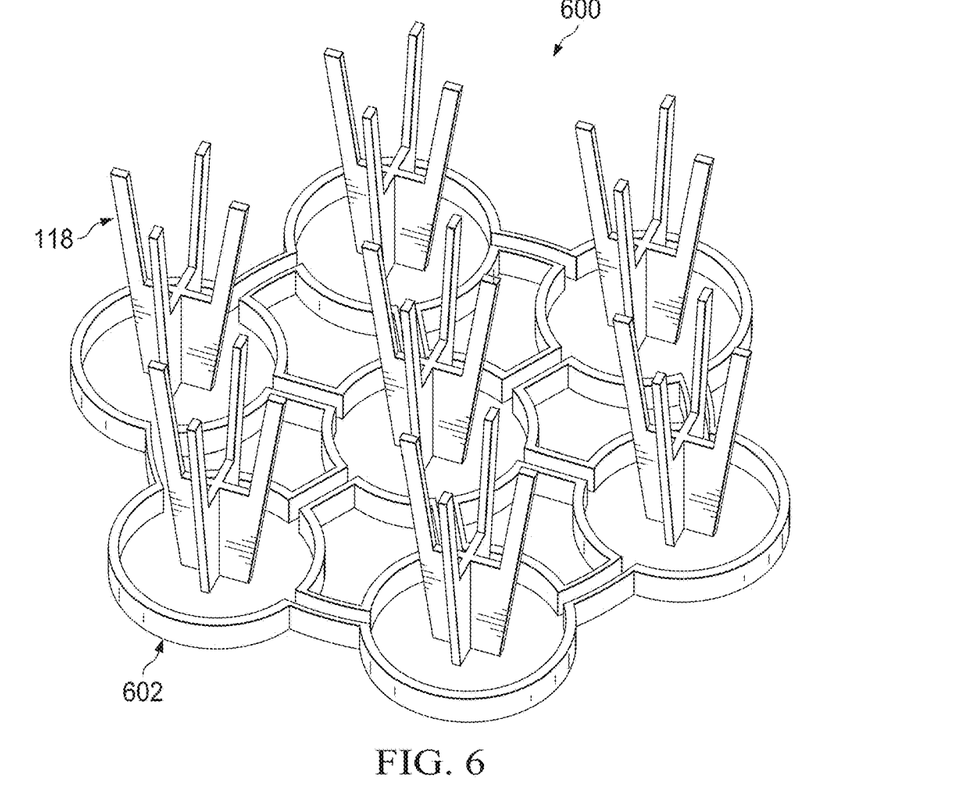
FIGS. 6 through 8 illustrate an example structure for holding personal protection equipment during thermo-chemical decontamination in accordance with this disclosure.
Figure 7:
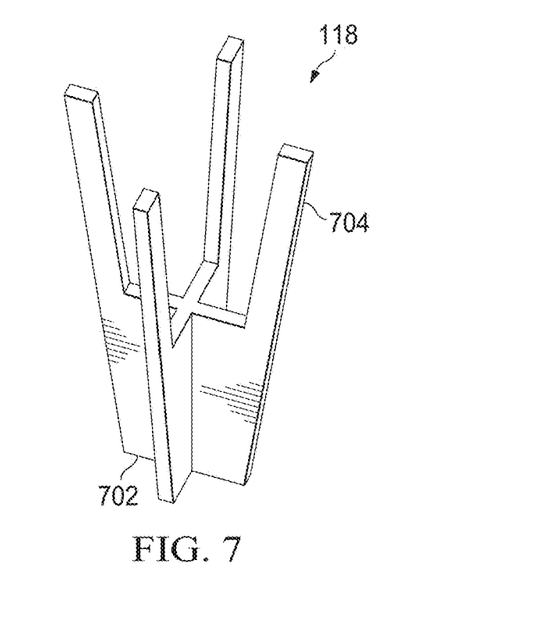
Figure 8:
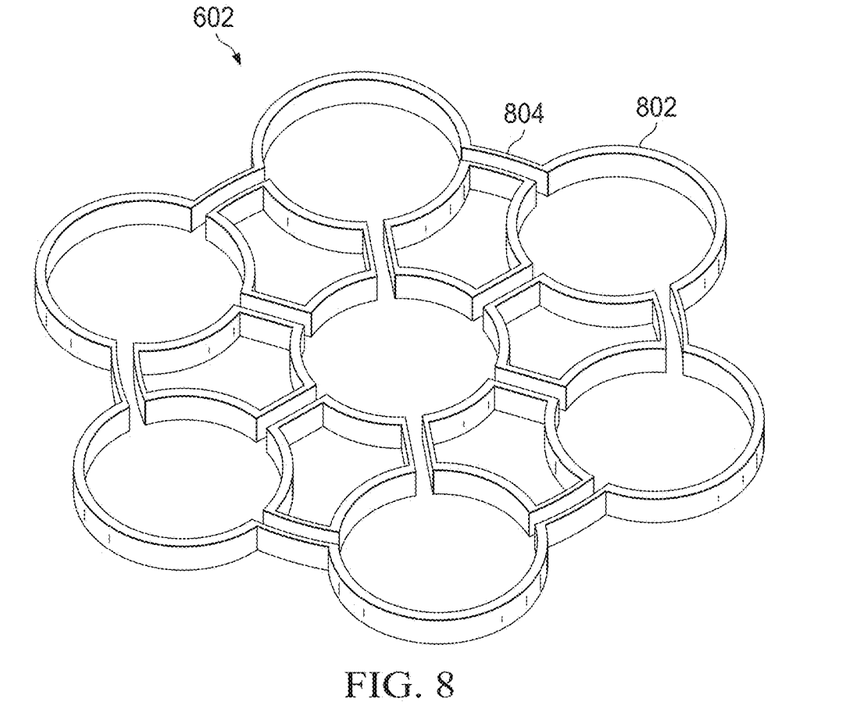

FIGS. 6 through 8 illustrate an example structure 600 for holding personal protection equipment during thermo-chemical decontamination in accordance with this disclosure. In particular, FIG. 6 illustrates an example arrangement of multiple stands 118 and an optional liquid holding area 602, where FIG. 7 illustrates the stand 118 and FIG. 8 illustrates the liquid holding area 602. As shown in FIG. 6, each of the stands 118 extends upward from the liquid holding area 602, and the stands 118 are configured to receive and hold masks or other personal protection equipment 120 above liquid. In some embodiments, the stands 118 are spaced equally or substantially equally apart in order to maintain adequate and more uniform spacing between the personal protection equipment 120. The liquid holding area 602 defines multiple areas in which the multiple stands 118 are placed and that hold a liquid (such as a low-concentration hydrogen peroxide solution or other disinfectant) under the personal protection equipment 120.

As can be seen in FIG. 7, each stand 118 includes a base portion 702 and multiple arms 704 extending upward from the base portion 702. The base portion 702 is configured to support the arms 704, and the arms 704 are configured to receive at least one piece of personal protection equipment 120 to be decontaminated. In this particular example, the base portion 702 has a cross-section in the form of a "+" sign, and each arm 704 has a cross-section in the form of a rectangle. This type of arrangement allows the stands 118 to contact and support the personal protection equipment 120 while covering very little surface area of the personal protection equipment 120, which can help to facilitate decontamination of the personal protection equipment 120. However, the base portion 702 and arms 704 may each have any other suitable cross-sectional shape. Also, while four arms 704 extend upward from the base portion 702 in this example, the stand 118 may include any other suitable number of arms 704.

As can be seen in FIG. 8, the liquid holding area 602 includes multiple reservoirs 802, each of which can be used to receive and hold liquid under personal protection equipment 120 placed on one of the stands 118. In this example, each reservoir 802 has a generally circular shape, although each reservoir 802 may have any other suitable shape. Also, there are seven reservoirs 802 here (associated with seven stands 118), although other numbers of stands 118 and reservoirs 802 may be used. Further, the layout and arrangement of the reservoirs 802 here are for illustration only. Channels 804 may optionally fluidly couple adjacent reservoirs 802 so that liquid can travel between different reservoirs 802 if needed. This may allow, for example, liquid in one reservoir 802 to be replenished with liquid from another reservoir 802 if the liquid vaporizes at different rates from the reservoirs 802 during heating.

Note that while not shown here, the stands 118 may be attached to the liquid holding area 602 to support the stands 118 and prevent the stands 118 from falling over. In these embodiments, each stand 118 may be attached to the liquid holding area 602 at one or more locations, and the attachments may be positioned or designed so as to not interfere with or block the flow of liquid between the reservoirs 802 through the channels 804 (assuming the channels 804 are present). Also note that while not shown here, the stands 118 and liquid holding area 602 themselves can be secured, integrated into, or attached to a lower base (such as a circular, rectangular, or other tray) that can be selectively inserted into and removed from the containment vessel 100, or the stands 118 and liquid holding area 602 themselves can be secured, integrated into, or attached to the lower surface of the body 102.

The stands 118 and the liquid holding area 602 may be formed from any suitable material(s), such as metal or ruggedized plastic. The stands 118 and the liquid holding area 602 may also be formed in any suitable manner, such as additive manufacturing, injection molding, casting, machining, or other suitable technique. The stands 118 and the liquid holding area 602 may each have any suitable size, shape, and dimensions.

Although FIGS. 6 through 8 illustrate one example structure 600 for holding personal protection equipment during thermo-chemical decontamination, various changes may be made to FIGS. 6 through 8. For example, the sizes, shapes, and dimensions of the components of the structure 600 can vary as needed or desired. Also, the number and placement of various components of the structure 600 can vary as needed or desired. Further, the structure 600 may be used to support or carry any number of pieces of personal protection equipment 120. In addition, the structure 600 may be used in any other suitable decontamination process and is not limited to the specific processes described above.

Figure 9:
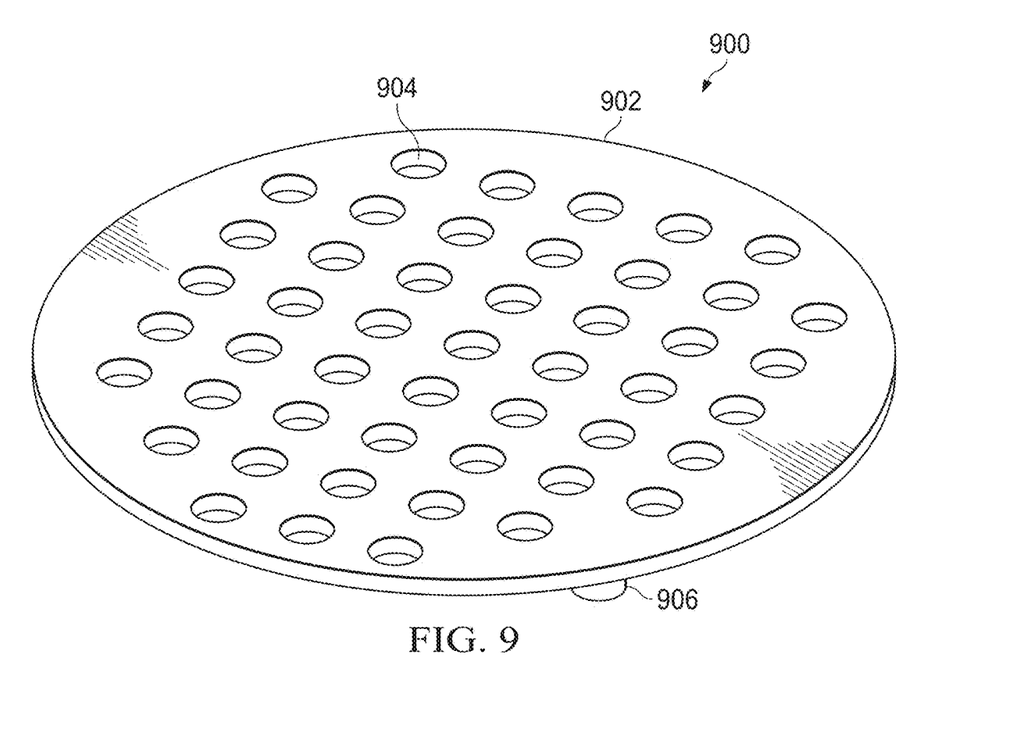
FIGS. 9 and 10 illustrate another example structure for holding personal protection equipment during thermo-chemical decontamination in accordance with this disclosure.
Figure 10:
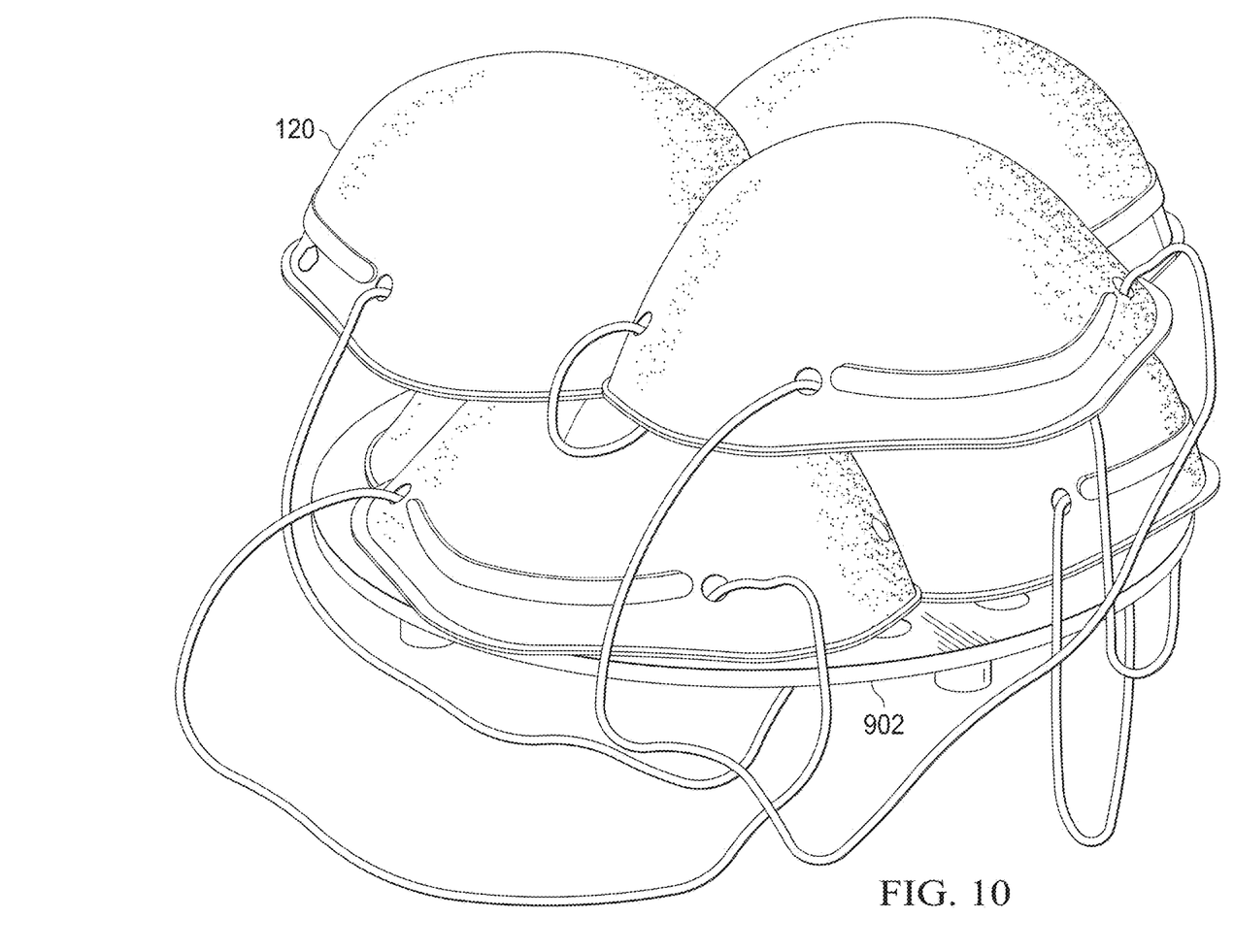

FIGS. 9 and 10 illustrate another example structure 900 for holding personal protection equipment during thermo-chemical decontamination in accordance with this disclosure. In particular, FIG. 9 illustrates the example structure 900, and FIG. 10 illustrates various pieces of personal protection equipment 120 placed on the structure 900. Note that the number and arrangement of the personal protection equipment 120 here are for illustration only.

As shown in FIG. 9, the structure 900 defines a substantially planar stand 902 onto which the personal protection equipment 120 can be stacked. The stand 902 includes multiple holes 904 and multiple standoffs 906. The holes 904 allow vaporized liquid (such as water and hydrogen peroxide or other disinfectant vapor) to travel from under the stand 902 to surround the personal protection equipment 120 during the decontamination process. The standoffs 906 elevate or help to hold the stand 902 above the bottom surface of the interior volume 106 of the containment vessel 100, which may provide space for at least one reservoir of liquid (if present).

In this example, the stand 902 is generally circular, although other shapes may be used. Each of the holes 904 may have any suitable size, shape, and dimensions, and any suitable number and arrangement of the holes 904 may be used in the stand 902. The holes 904 may also be formed in the stand 902 in any suitable manner, such as by etching or otherwise forming the holes 904 in an already-formed stand 902 or by forming the stand 902 to include the holes 904. The standoffs 906 can be formed from any suitable material(s) and in any suitable manner. The standoffs 906 may be formed integral with the stand 902 or formed separate from and attached to the stand 902.

Note that, depending on the size of the containment vessel 100, it might be possible to use multiple instances of the structure 900 to hold multiple layers of personal protection equipment 120 in the containment vessel 100. For example, in some embodiments, the lowest structure 900 may be separated from the bottom surface of the interior volume 106 using standoffs 906 that are relatively short. Each higher structure 900 may be separated from a lower structure 900 using taller standoffs. In other embodiments, at least some of the structures 900 may rest on brackets that project inward from the inner wall(s) of the interior volume 106, and each lower structure 900 may be sized or shaped to move past brackets for higher structures 900 or may include slots that allow that structure 900 to pass around the brackets for higher structures 900. However, any other suitable mechanism may be used here to support or separate multiple instances of the structures 900.

Although FIGS. 9 and 10 illustrate another example structure 900 for holding personal protection equipment during thermo-chemical decontamination, various changes may be made to FIGS. 9 and 10. For example, the sizes, shapes, and dimensions of the components of the structure 900 can vary as needed or desired. Also, the number and placement of various components of the structure 900 can vary as needed or desired. Further, the structure 900 may be used to support or carry any number of pieces of personal protection equipment 120. In addition, the structure 900 may be used in any other suitable decontamination process and is not limited to the specific processes described above.

Figure 11:
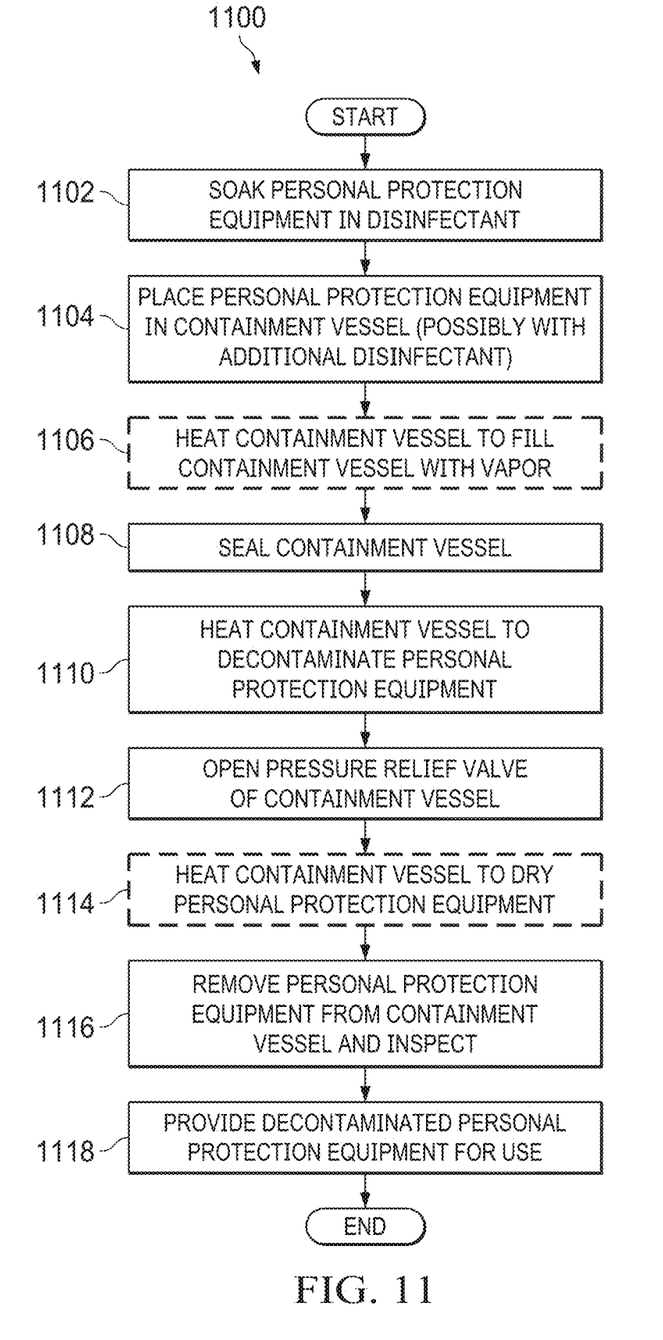
FIG. 11 illustrates an example method for low-cost rapid thermo-chemical decontamination of personal protection equipment in accordance with this disclosure.

FIG. 11 illustrates an example method 1100 for low-cost rapid thermo-chemical decontamination of personal protection equipment in accordance with this disclosure. For ease of explanation, the method 1100 is described as being performed using the containment vessel 100 of FIGS. 1 through 4. However, the method 1100 may be performed using any suitable containment vessel designed in accordance with this disclosure.

As shown in FIG. 11, one or more pieces of personal protection equipment are soaked in a disinfectant at step 1102. This may include, for example, personnel soaking one or more pieces of personal protection equipment 120 in a low-concentration hydrogen peroxide solution (such as an about 3% to about 6% hydrogen peroxide solution or other hydrogen peroxide solution) or other disinfectant that is safe for everyday use. The one or more pieces of personal protection equipment are placed within a containment vessel at step 1104. This may include, for example, the personnel placing the one or more pieces of personal protection equipment 120 onto one or more stands 118 or 902.

The containment vessel may optionally be heated to at least partially fill an interior of the containment vessel with vapor at step 1106. This may include, for example, the personnel attaching the lid 104 to the body 102 and opening the pressure-relief valve 110 of the containment vessel 100. This may also include the personnel using a microwave oven or other heat source to heat the containment vessel 100, causing at least some of the low-concentration hydrogen peroxide solution or other disinfectant to vaporize. Since this occurs while the pressure-relief valve 110 of the containment vessel 100 is opened, this allows the vapor to replace at least some of the air inside the containment vessel 100.

The containment vessel is sealed at step 1108, and the containment vessel is heated to decontaminate the one or more pieces of personal protection equipment at step 1110. This may include, for example, the personnel attaching the lid 104 to the body 102 (if not already done) and closing the pressure-relief valve 110 of the containment vessel 100, which seals the interior volume 106 of the containment vessel 100. This may also include the personnel using the microwave oven or other heat source to heat the containment vessel 100, which heats the one or more pieces of personal protection equipment 120 and the low-concentration hydrogen peroxide solution or other disinfectant within the containment vessel 100. In some cases, the personal protection equipment 120 is heated to be within a suitable range, such as about 65° C. to about 80° C. (like about 70° C.), to prevent damage to the personal protection equipment 120 or degradation of the personal protection equipment's fit or function while being adequate to decontaminate the personal protection equipment 120.

Once the heating process is completed, the pressure-relief valve of the containment vessel is opened at step 1112. This may include, for example, the personnel opening the pressure-relief valve 110 of the containment vessel 100, which unseals the interior volume 106 of the containment vessel 100. Optionally, the containment vessel can be heated again to dry the one or more pieces of personal protection equipment at step 1114. This may include, for example, the personnel using the microwave oven or other heat source to heat the containment vessel 100, which heats the one or more pieces of personal protection equipment 120 and the moisture within the containment vessel 100 and allows the moisture to escape the containment vessel 100 through the pressure-relief valve 110. In some cases, the personal protection equipment 120 is heated to be within a suitable range, which may or may not be the same as the range used for decontamination purposes.

The one or more pieces of personal protection equipment are removed from the containment vessel and can be inspected at step 1116. This may include, for example, the personnel removing the lid 104 from the body 102 of the containment vessel 100 and removing the one or more pieces of personal protection equipment 120 from the stands 118 or 902. This may also include the personnel inspecting the one or more pieces of personal protection equipment 120 for any damage or other issues that might negatively impact the effectiveness of the personal protection equipment 120. The personal protection equipment, now decontaminated, can be provided to one or more users for use at step 1118.

Although FIG. 11 illustrates one example of a method 1100 for low-cost rapid thermo-chemical decontamination of personal protection equipment, various changes may be made to FIG. 11. For example, while shown as a series of steps, various steps in FIG. 11 may overlap, occur in parallel, occur in a different order, or occur any number of times. Also, any suitable steps may be added or omitted according to particular needs. As a particular example, the personal protection equipment may be dried in any other suitable manner.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present disclosure should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A method comprising:
   soaking one or more pieces of personal protection equipment in a disinfectant;
   placing the one or more soaked pieces of personal protection equipment within a containment vessel;
   heating the containment vessel to allow air in the containment vessel to escape through a pressure-relief valve and be substantially replaced with vapor;
   sealing the one or more soaked pieces of personal protection equipment within the containment vessel by closing the pressure-relief valve;
   decontaminating the one or more soaked pieces of personal protection equipment by heating the one or more soaked pieces of personal protection equipment in the sealed containment vessel;
   protruding a microwave-safe indicator from a surface of the containment vessel when the decontamination is completed; and
   opening the pressure-relief valve of the containment vessel.

2. The method of claim 1, further comprising:
   drying the one or more decontaminated pieces of personal protection equipment by reheating the one or more decontaminated pieces of personal protection equipment in the containment vessel.

3. The method of claim 2, wherein, when drying the one or more decontaminated pieces of personal protection equipment, water and disinfectant escape the containment vessel through the pressure-relief valve.

4. The method of claim 1, wherein the disinfectant comprises an about 3% to about 6% hydrogen peroxide solution.

5. The method of claim 1, wherein heating the one or more soaked pieces of personal protection equipment in the sealed containment vessel comprises heating the one or more soaked pieces of personal protection equipment to a temperature of about 65° C. to about 80° C.

6. The method of claim 1, wherein heating the one or more soaked pieces of personal protection equipment in the sealed containment vessel comprises heating the one or more soaked pieces of personal protection equipment to a temperature of about 70° C.

7. The method of claim 1, wherein heating the one or more soaked pieces of personal protection equipment in the sealed containment vessel comprises using a microwave oven.

8. The method of claim 1, wherein the one or more pieces of personal protection equipment comprise at least one of: one or more facemasks, one or more surgical gowns, one or more gloves, and one or more surgical booties.

* * * * *